(12) United States Patent
Philip

(10) Patent No.: US 10,144,766 B2
(45) Date of Patent: Dec. 4, 2018

(54) CYTOTOXIC T LYMPHOCYTE INDUCING IMMUNOGENS FOR PREVENTION TREATMENT AND DIAGNOSIS OF DENGUE VIRUS INFECTION

(71) Applicant: Emergex Vaccines Holdings Limited, Abingdon, Oxfordshire (GB)

(72) Inventor: Ramila Philip, Ivyland, PA (US)

(73) Assignee: Emergex Vaccines Holding Ltd., Abingdon, Oxford (GB)

( * ) Notice: Subject to any disclaimer, the term of this patent is extended or adjusted under 35 U.S.C. 154(b) by 0 days.

(21) Appl. No.: 15/471,098

(22) Filed: Mar. 28, 2017

(65) Prior Publication Data
US 2017/0275338 A1    Sep. 28, 2017

Related U.S. Application Data

(63) Continuation of application No. 14/116,899, filed as application No. PCT/US2012/044625 on Jun. 28, 2012, now Pat. No. 9,637,521.

(60) Provisional application No. 61/502,365, filed on Jun. 29, 2011.

(51) Int. Cl.
| | |
|---|---|
| *A61K 39/00* | (2006.01) |
| *A61K 39/12* | (2006.01) |
| *A61K 39/145* | (2006.01) |
| *C07K 14/005* | (2006.01) |
| *A61K 39/085* | (2006.01) |
| *A61K 38/01* | (2006.01) |
| *A61K 38/19* | (2006.01) |

(52) U.S. Cl.
CPC .......... *C07K 14/005* (2013.01); *A61K 38/017* (2013.01); *A61K 38/19* (2013.01); *A61K 39/12* (2013.01); *A61K 2039/55522* (2013.01); *C12N 2770/24134* (2013.01); *Y02A 50/386* (2018.01)

(58) Field of Classification Search
CPC .... A61K 39/12; A61K 2300/00; A61K 39/00; A61K 2039/55522; C07K 14/005
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,690,915 A | 9/1987 | Rosenberg | |
| 4,722,848 A | 2/1988 | Paoletti et al. | |
| 4,837,028 A | 6/1989 | Allen | |
| 4,844,893 A | 7/1989 | Honski et al. | |
| 5,019,369 A | 5/1991 | Presant et al. | |
| 5,635,363 A | 6/1997 | Altmann et al. | |
| 2008/0107668 A1 | 5/2008 | Philip et al. | |
| 2012/0141579 A1 | 6/2012 | Philip | |
| 2014/0105925 A1 | 4/2014 | Philip | |
| 2014/0220117 A1 | 8/2014 | Philip | |

FOREIGN PATENT DOCUMENTS

WO    WO2009152147    * 12/2009

OTHER PUBLICATIONS

Bertoni et al., J Clin Invest., 100(3);503-513, 1997.
Slovin SF, Lackman RD, Ferrone S, Kiely PE, Mastraugelo MJ. Cellular immune response to human sarcomas: cytotoxic T cell clones reactive with autologous sarcomas. I. Development, phenotype, and specificity. J Immunol. 1986;137(9):3042-8. Epub Nov. 1, 1986. PubMed PMID: 3093588.
Schendel DJ, Gansbacher B, Oberneder R, Knegmair M, Hofstetter A, Riethmuller G, et al. Tumor-specific lysis of human renal cell carcinomas by tumor-infiltrating lymphocytes. I. HLA-A2-restricted recognition of autologous and allogeneic tumor lines. J Immunol. 1993;151(8):4209-20. Epub Oct. 15, 1993. PubMed PMID: 8409397.
Jacob L, Somasundaram R, Smith W, Monos D, Basak S, Marincola F, et al. Cytotoxic T-cell clone against rectal carcinoma induced by stimulation of a patient's peripheral blood mononuclear cells with autologous cultured tumor cells. Int J Cancer. 1997;71(3):325-32. Epub May 2, 1997. PubMed PMID: 9139862.
Ioannides CG, Freedman RS, Platsoucas CD, Rashed S, Kim YP. Cytotoxic T cell clones isolated from ovarian tumor-infiltrating lymphocytes recognize multiple antigenic epitopes on autologous tumor cells. J Immunol. 1991;146(5):1700-7. Epub Mar. 1, 1991. PubMed PMID: 1704404.
Peoples GE, Schoof DD, Andrews JV, Goedegebuure PS, Eberlein TJ. T-cell recognition of ovarian cancer. Surgery. 1993;114(2):227-34. Epub Aug. 1, 1993. PubMed PMID: 8342128.
Peiper M, Goedegebuure PS, Linehan DC, Ganguly E, Douville CC, Eberlein TJ. The HER2/neu-derived peptide p654-662 is a tumor-associated antigen in human pancreatic cancer recognized by cytotoxic T lymphocytes. Eur J Immunol. 1997:27(5):1115-23. Epub May 1, 1997. doi: 10.1002/eji.1830270511. PubMed PMID: 9174600.

(Continued)

*Primary Examiner* — Barry A Chestnut
(74) *Attorney, Agent, or Firm* — Joseph F. Aceto, Esq.

(57) ABSTRACT

Dengue Fever (DF) and Dengue Hemorrhagic Fever (DHR) are significant global public health problems and understanding the overall immune response to infection will contribute to appropriate management of the disease and its potentially severe complications. Live attenuated and subunit vaccine candidates, which are under clinical evaluation, induce primarily an antibody response to the virus and minimal cross-reactive T cell responses. Currently, there are no available tools to assess protective T cell responses during infection or post vaccination. The present invention incorporates immunoproteomics to uncover novel HLA-A2 specific epitopes derived from Dengue Virus (DV)-infected cells. These epitopes are conserved with epitope-specific CTLs cross-reacting against all four DV serotypes. These epitopes have potential as new informational and diagnostic tools to characterize T cell immunity in Dengue virus (DV) infection, and serves as a universal vaccine candidate complementary to current vaccines.

19 Claims, 8 Drawing Sheets
Specification includes a Sequence Listing.

(56) References Cited

OTHER PUBLICATIONS

Wolfel T, Herr W, Coulie P, Schmitt U, Meyer Zum Buschenfelde KH, Knuth A. Lysis of human pancreatic adenocarcinoma cells by autologous HLA-class I-restricted cytolytic T-lymphocyte (CTL) clones. Int J Cancer. 1993;54(4):636-44. Epub Jun. 19, 1993. PubMed PMID: 8514455.
Yasumura S, Hirabayashi H, Schwartz DR, Toso JF, Johnson JT, Herberman RB, et al. Human cytotoxic T-cell lines with restricted specificity for squamous cell carcinoma of the head and neck. Cancer Res. 1993;53(6):1461-8. Epub Mar. 15, 1993. PubMed PMID: 8443824.
Slinglluff CL, Jr., Cox AL, Stover JM, Jr., Moore MM, Hunt DF, Engelhard VH. Cytotoxic T-lymphocyte response to autologous human squamous cell cancer of the lung: epitope reconstitution with peptides extracted from HLA-Aw68. Cancer Res. 1994;54(10):2731-7. Epub May 15, 1994. PubMed PMID: 7513255.
Yoshino I, Goedegebuure PS, Peoples GE, Parikh AS, DiMaio JM, Lyerly HK, et al. HER2/neu-derived peptides are shared antigens among human non-small cell lung cancer and ovarian cancer. Cancer Res. 1994;54(13):3387-90. Epub Jul. 1, 1994. PubMed PMID: 7912166.
Boon T, Cerottini JC, Van Den Eynde B, Van Der Bruggen P, Vanpela. Tumor antigens recognized by T lymphocytes. Annu Rev Immunol. 1994;12:337-65. Epub Jan. 1, 1994. doi: 10.1146/annurev. iy.12.040194.002005. PubMed PMID: 8011285.
Rosenberg SA, Packard BS, Aebersold PM, Solomon D, Topalian SL, Toy ST, et al. Use of tumor-infiltrating lymphocytes and interleukin-2 in the immunotherapy of patients with metastatic melanoma. A preliminary report. N Engl J Med. 1988;319(25):1676-80. Epub Dec. 22, 1988. doi: 10.1056/NEJM198812223192527. PubMed PMID: 3264384.
Celluzzi CM, Mayordomo JI, Storkus WJ, Lotze MT, Falo LD, Jr. Peptide-pulsed dendritic cells induce antigen-specific CTL-mediated protective tumor immunity. J Exp Med. 1996;183(1):283-7. Epub Jan. 1, 1996. PubMed PMID: 8551233; PubMed Central PMCID: PMC2192396.
Mayordomo JI, Zorina T, Storkus WJ, Zitvogel L, Celluzzi C, Falo LD, et al. Bone marrow-derived dendritic cells pulsed with synthetic tumour peptides elicit protective and therapeutic antitumour immunity. Nat Med. 1995;1(12):1297-302. Epub Dec. 1, 1995. PubMed PMID: 7489412.
Zitvogel L, Mayordomo JI, Tjandrawan T, DeLeo AB, Clarke MR, Lotze MT, et al. Therapy of murine tumors with tumor peptide-pulsed dendritic cells: dependence on T cells, B7 costimulation, and T helper cell 1-associated cytokines. J Exp Med. 1996;183(1):87-97. Epub Jan. 1, 1996. PubMed PMID: 8551248; PubMed Central PMCID: PMC2192415.
Rock KL, Goldberg AL. Degradation of cell proteins and the generation of MHC class I-presented peptides. Annu Rev Immunol. 1999;17:739-79. Epub Jun. 8, 1999. doi: 10.1146/annurev.immunol. 17.1.739. PubMed PMID: 10358773.
Watts C. Capture and processing of exogenous antigens for presentation on MHC molecules. Annu Rev Immunol. 1997;15:821-50. Epub Jan. 1, 1997. doi: 10.1146/annurev.immunol.15.1.821. PubMed PMID: 9143708.
Rosenberg SA. A new era for cancer immunotherapy based on the genes that encode cancer antigens. Immunity. 1999;10(3):281-7. Epub Apr. 16, 1999. PubMed PMID: 10204484.
Gilboa E. The makings of a tumor rejection antigen. Immunity. 1999;11(3):263-70. Epub Oct. 8, 1999. PubMed PMID: 10514004.
Yewdell JW, Bennink JR. Mechanisms of viral interference with MHC class I antigen processing and presentation. Annual review of cell and developmental biology. 1999;15:579-606. Epub Dec. 28, 1999. doi: 10.1146/annurev.cellbio.15.1.579. PubMed PMID: 10611973.
Henderson RA, Cox AL, Sakaguchi K, Appella E, Shabanowitz J, Hunt DF, et al. Direct identification of an endogenous peptide recognized by multiple HLA-A2.1-specific cytotoxic T cells. Proc Natl Acad Sci U S A. 1993;90(21):10275-9. Epub Nov. 1, 1993. PubMed PMID: 7694286; PubMed Central PMCID: PMC47757.
Hogan KT, Eisinger DP, Cupp SB, 3rd, Lekstrom KJ, Deacon DD, Shabanowitz J, et al. The peptide recognized by HLA-A68.2-restricted, squamous cell carcinoma of the lung-specific cytotoxic T lymphocytes is derived from a mutated elongation factor 2 gene. Cancer Res. 1998;58(22):5144-50. Epub Nov. 21, 1998. PubMed PMID: 9823325.
Hunt DF, Henderson RA, Shabanowitz J, Sakaguchi K, Michel H, Sevilir N, et al. Characterization of peptides bound to the class I MHC molecule HLA-A2.1 by mass spectrometry. Science. 1992;255(5049):1261-3. Epub Mar. 6, 1992. PubMed PMID: 1546328.
Slingluff CL, Jr., Cox AL, Henderson RR, Hunt DF, Engelhard VH. Recognition of human melanoma cells by HLA-A2.1-restricted cytotoxic T lymphocytes is mediated by at least six shared peptide epitopes. J Immunol. 1993;150(7):2955-63. Epub Apr. 1, 1993. PubMed PMID: 7681084.
Grant GA. Synthetic Peptides: A User's Guide. New York: W. H. Freeman and Company; 1992.
Coligan JE. Current Protocols in Protein Science. New York: John Wiley & Sons, Inc.; 1999.
Ausubel FM. Current Protocols in Molecular Biology. New York: John Wiley & Sons, Inc.; 1999.
Molecular Cloning: A Laboratory Manual. Cold Spring Harbor: Cold Spring Harbor Laboratory Press; 1989.
Posnett DN, McGrath H, Tam JP. A novel method for producing anti-peptide antibodies. Production of site-specific antibodies to the T cell antigen receptor beta-chain. J Biol Chem. 1988;263(4):1719-25. Epub Feb. 5, 1988. PubMed PMID: 3276675.
Parkhurst MR, Salgaller ML, Southwood S, Robbins PF, Setto A, Rosenberg SA, et al. Improved induction of melanoma-reactive CTL with peptides from the melanoma antigen gp100 modified at HLA-A*0201-binding residues. J Immunol. 1996;157(6):2539-48. Epub Sep. 15, 1996. PubMed PMID: 8805655.
Rosenberg SA, Yang JC, Schwartzentruber DJ, Hwu P, Marincola FM, Topalian SL, et al. Immunologic and therapeutic evaluation of a synthetic peptide vaccine for the treatment of patients with metastatic melanoma. Nat Med. 1998;4(3):321-7. Epub Mar. 21, 1998. PubMed PMID: 9500606; PubMed Central PMCID: PMC2064864.
Gluzman Y. SV40-transformed simian cells support the replication of early SV40 mutants. Cell. 1981;23(1):175-82. Epub Jan. 1, 1981. PubMed PMID: 6260373.
Ljunggren HG, Siam NJ, Ohlen C, Neefjes JJ, Hoglund P, Heemels MT, et al. Empty MHC class I molecules come out in the cold. Nature. 1990;346(6283):476-80. Epub Aug. 2, 1990. doi: 10.1038/346476a0. PubMed PMID: 2198471.
Zeh HJ, 3rd, Leder GH, Lotze MT, Salter RD, Tector M, Stuber G, et al. Flow-cytometric determination of peptide-class I complex formation. Identification of p53 peptides that bind to HLA-A2. Hum Immunol. 1994;39(2):79-86. Epub Feb. 1, 1994. PubMed PMID: 8175386.
Riddell SR, Greenberg PD. The use of anti-CD3 and anti-CD28 monoclonal antibodies to clone and expand human antigen-specific T cells. J Immunol Methods. 1990;128(2):189-201. Epub Apr. 17, 1990. PubMed PMID: 1691237.
Walter EA, Greenberg PD, Gilbert MJ, Finch RJ, Watanabe KS, Thomas ED, et al. Reconstitution of cellular immunity against cytomegalovirus in recipients of allogeneic bone marrow by transfer of T-cell clones from the donor. N Engl J Med. 1995;333(16):1038-44. Epub Oct. 19, 1995. doi: 10.1056/NEJM199510193331603. PubMed PMID: 7675046.
Harding CV, 3rd. Electroporation of exogenous antigen into the cytosol for antigen processing and class I major histocompatibility complex (MHC) presentation: weak base amines and hypothermia (18 degrees C) inhibit the class I MHC processing pathway. Eur J Immunol. 1992;22(7):1865-9. Epub Jul. 1, 1992. doi: 10.1002/eji. 1830220728. PubMed PMID: 1623927.
Reddy R, Zhou F, Huang L, Carbone F, Bevan M, Rouse BT. pH sensitive liposomes provide an efficient means of sensitizing target cells to class I restricted CTL recognition of a soluble protein. J Immunol Methods. 1991;141(2):157-63. Epub Aug. 9, 1991. PubMed PMID: 1880423.

(56) References Cited

OTHER PUBLICATIONS

Moore MW, Carbone FR, Bevan MJ. Introduction of soluble protein into the class I pathway of antigen processing and presentation. Cell. 1988;54(6):777-85. Epub Sep. 9, 1988. PubMed PMID: 3261634.

Tuting T, Wilson CC, Martin DM, Kasamon YL, Rowles J, Ma DI, et al. Autologous human monocyte-derived dendritic cells genetically modified to express melanoma antigens elicit primary cytotoxic T cell responses in vitro: enhancement by cotransfection of genes encoding the Th1-biasing cytokines IL-12 and IFN-alpha. J Immunol. 1998;160(3):1139-47. Epub May 7, 1998. PubMed PMID: 9570527.

Perez-Diez A, Butterfield LH, Li L, Chakraborty NG, Economou JS, Mukherji B. Generation of CD8+ and CD4+ T-cell response to dendritic cells genetically engineered to express the MART-1/Melan-A gene. Cancer Res. 1998;58(23):5305-9. Epub Dec. 16, 1998. PubMed PMID: 9850054.

North RJ, LaCourse R, Ryan L. Vaccinated mice remain more susceptible to *Mycobacterium tuberculosis* infection initiated via the respiratory route than via the intravenous route. Infect Immun. 1999;67(4):2010-2. Epub Mar. 20, 1999. PubMed PMID: 10085050; PubMed Central PMCID: PMC96560.

Riddell SR, Watanabe KS, Goodrich JM, Li CR, Agha ME, Greenberg PD. Restoration of viral immunity in immunodeficient humans by the adoptive transfer of T cell clones. Science. 1992;257(5067):238-41. Epub Jul. 10, 1992. pubMed PMID: 1352912.

Ramakrishna V, Ross MM, Pettersson M, Gatlin CC, Lyons CE, Miller CL, et al. Naturally occurring peptides associated with HLA-A2 in ovarian cancer cell lines identified by mass spectrometry are targets of HLA-A2-restricted cytotoxic T cells. Int Immunol. 2003;15(6):751-63. Epub May 17, 2003. PubMed PMID: 12750359.

Morse MA, Nair SK, Mosca PJ, Hobeika AC, Clay TM, Deng Y, et al. Immunotherapy with autologous, human dendritic cells transfected with carcinoembryonic antigen mRNA. Cancer Invest. 2003;21(3):341-9. Epub Aug. 7, 2003. PubMed PMID: 12901279.

Hanahan D, Weinberg RA. The hallmarks of cancer. Cell. 2000;100(1):57-70. Epub Jan. 27, 2000. PubMed PMID: 10647931.

Yewdell, J. W. and Bennink, J. R., Ann.Rev.Immunol., 17:51-88, (1999).

Henderson, R. A. et al., Proc.Natl.Acad.Sci.U.S.A, 90:10275-10279, (1993).

Posneft, D. N. et al., J.Biol.Chem., 263:1719-1725, (1988).

James S. Testa, et al. J Infect Dis 205(4): 647-655. (2012).

\* cited by examiner

Fig. 2 A
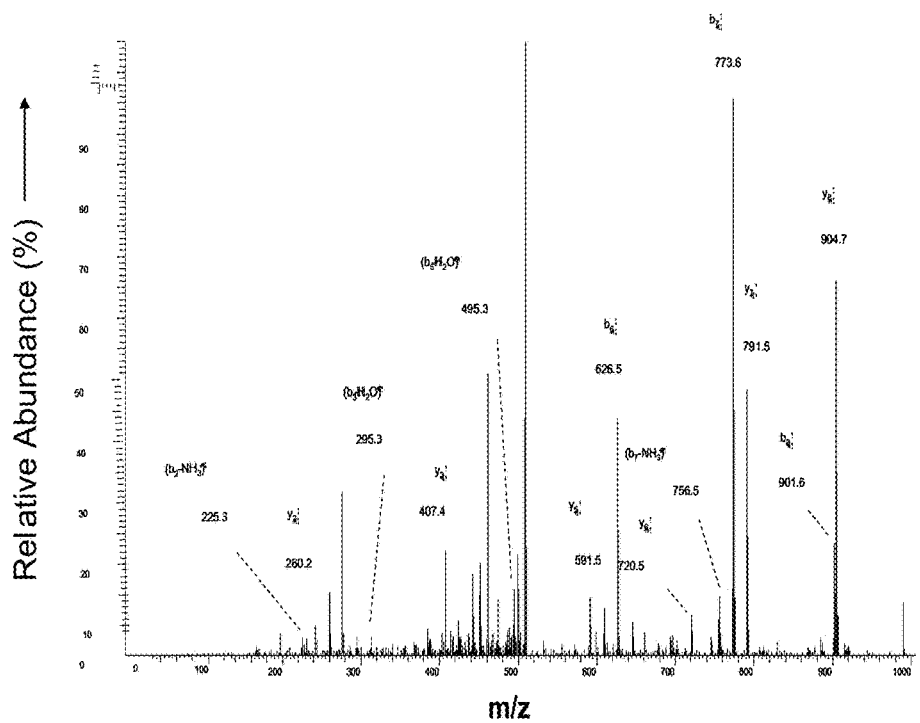
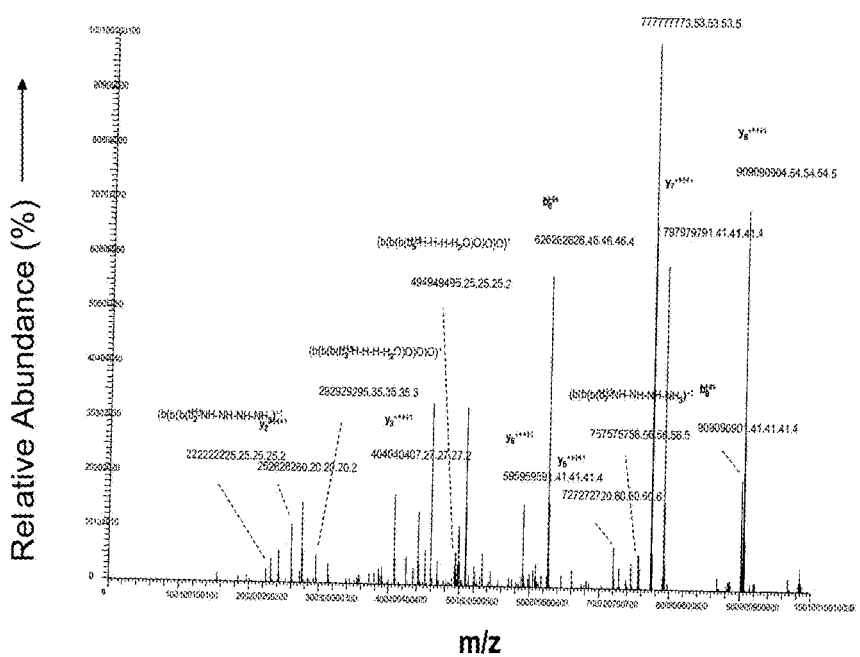

Fig. 2 B
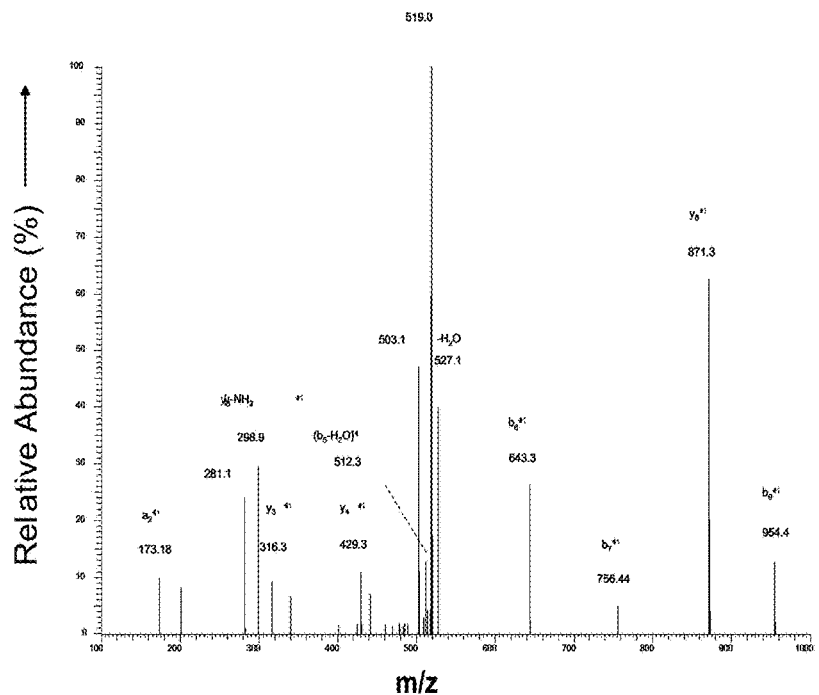
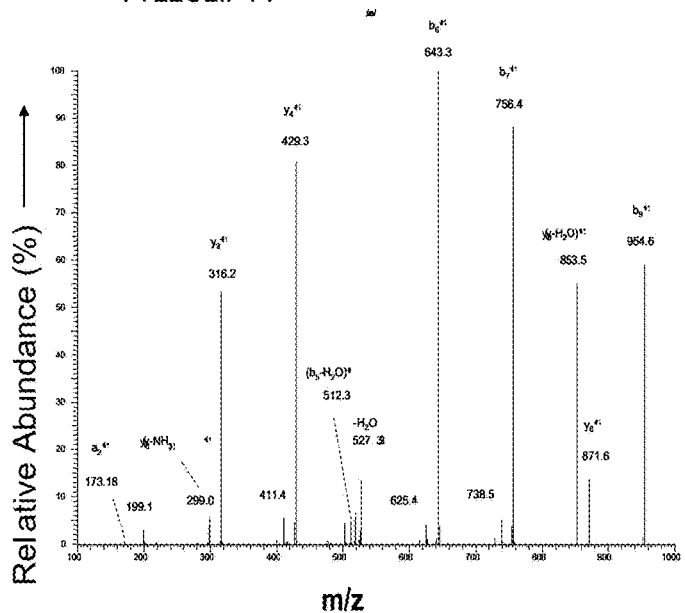

Fig. 2 C
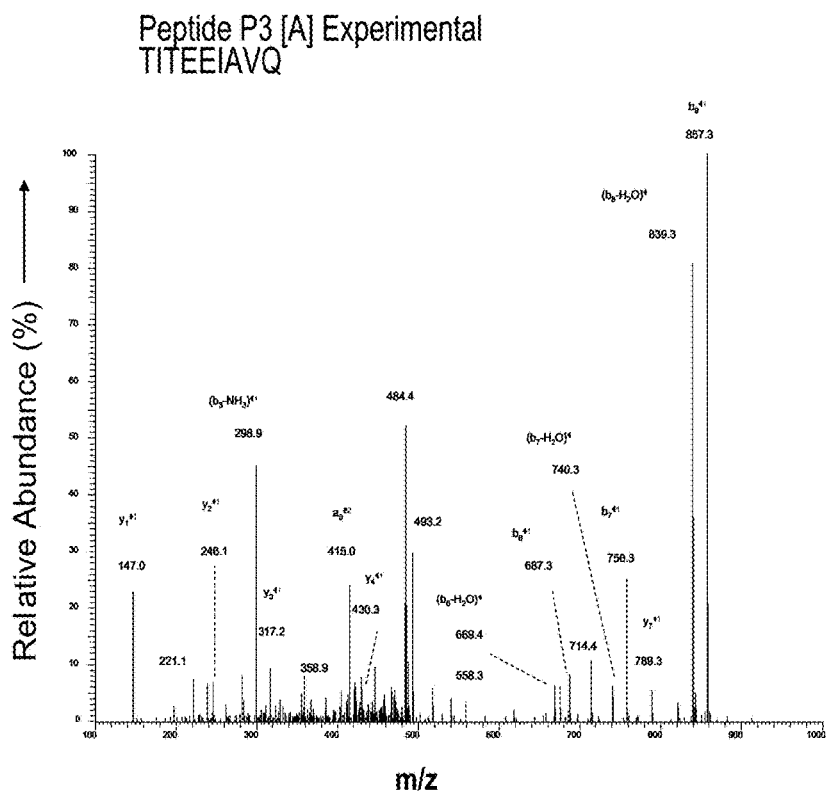
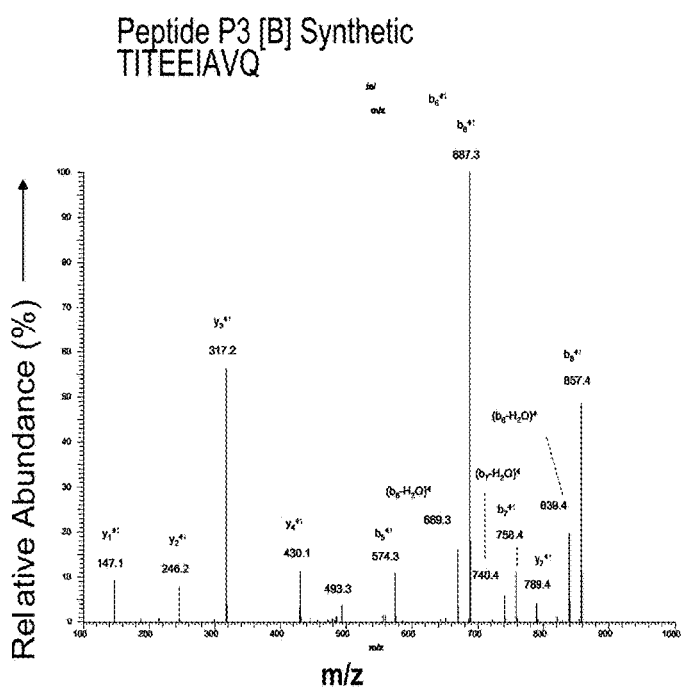

Fig. 2 D
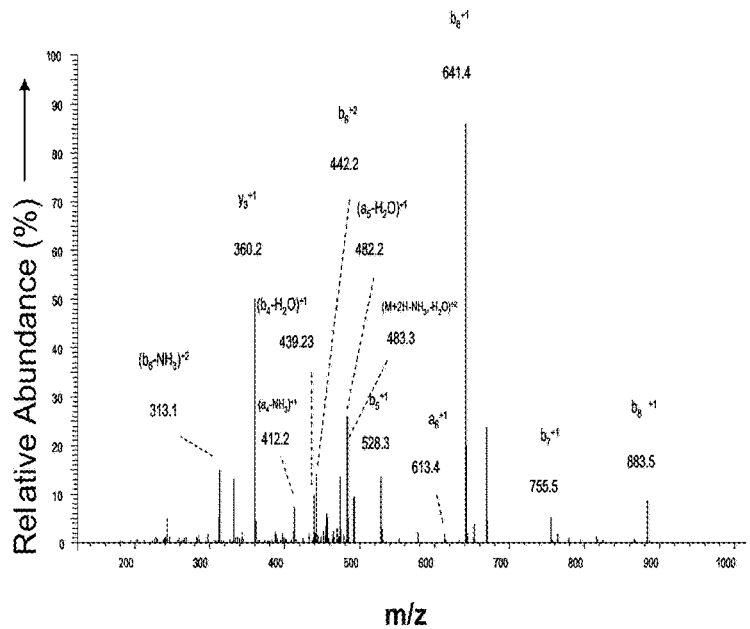
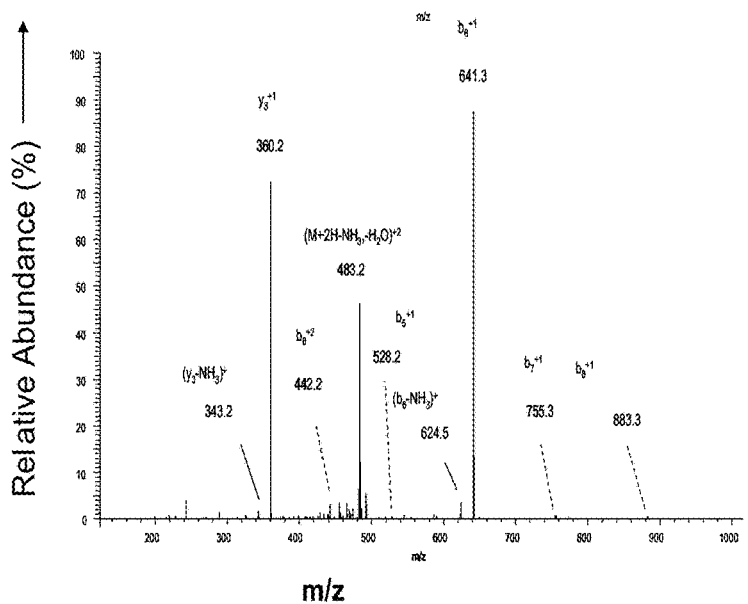

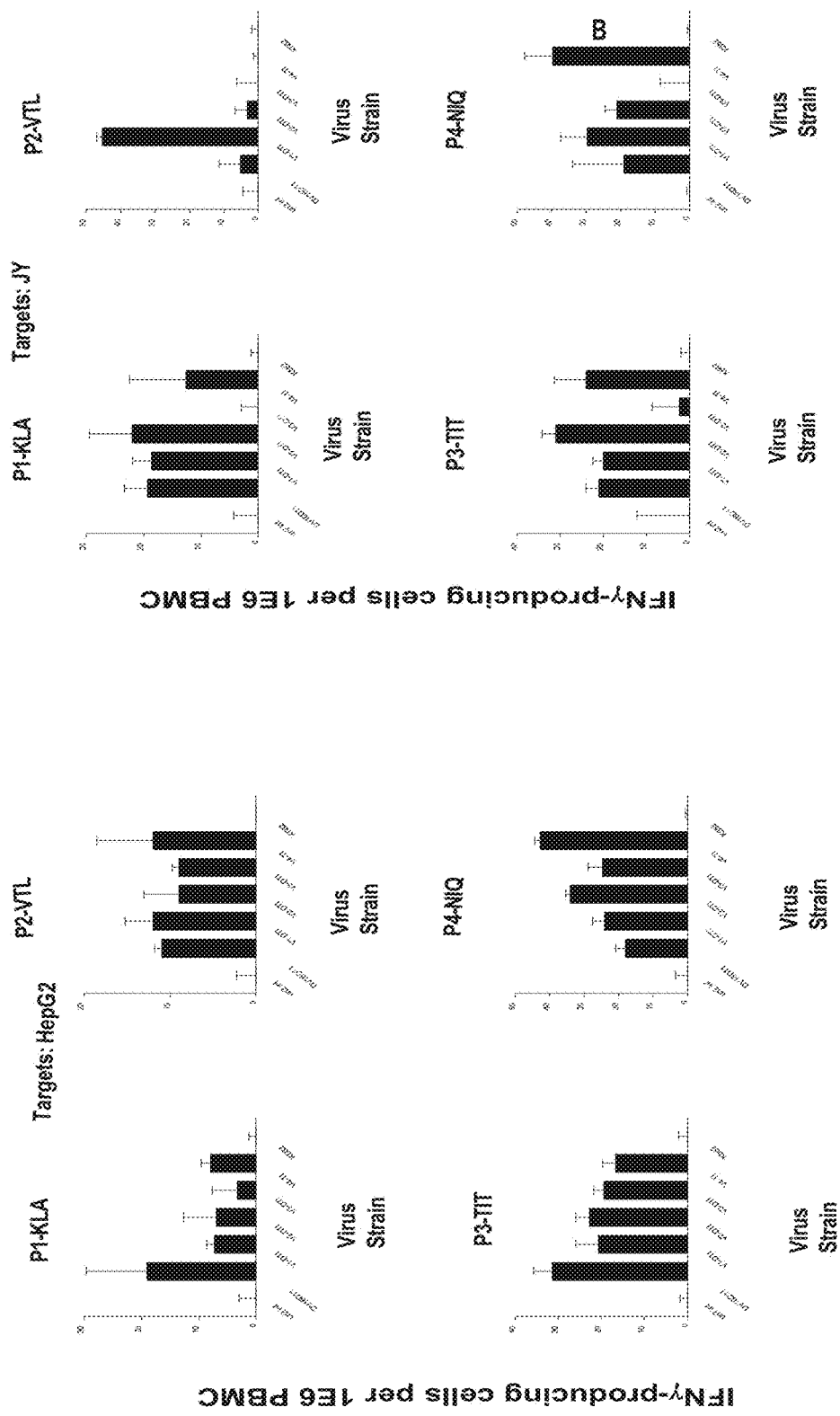

CYTOTOXIC T LYMPHOCYTE INDUCING IMMUNOGENS FOR PREVENTION TREATMENT AND DIAGNOSIS OF DENGUE VIRUS INFECTION

CROSS REFERENCE TO RELATED APPLICATIONS

This application is a continuation of US national application 14/116, filed on 29 Dec. 2014 now allowed, which is the US national phase application of PCT/US2012/044625, filed on 28 Jun. 2012 and which claims priority to U.S. Provisional Application No. 61/502,365, filed on 29 Jun. 2011, the disclosure of which is herein incorporated by reference in its entirety.

This invention was made with Government support under Grant Number A1062177 awarded by the National Institutes of Health, The Government has certain rights in the invention.

FIELD OF THE INVENTION

The present invention relates generally to the field of immunogens whose structures incorporate polypeptides comprising epitopic peptides derived from proteins expressed by dengue virus (DV 1-4) infected cells and uses of said immunogens in eliciting cytotoxic T lymphocyte (CTL) responses for the diagnosis, prevention and treatment of all 4 serotypes of dengue virus infection.

BACKGROUND OF THE INVENTION

Dengue Fever (DF) and Dengue Hemorrhagic Fever (DHF) are significant public health problems internationally, and caused by four antigenically distinct serotypes of dengue virus (DV1-4). Approximately 36 million cases of DF and 2.1 million cases of DHF occur annually and 2.5-3.5 billion of the world population are at risk of transmission of DF. Although patients who have recovered from DV infection are immune to re-challenge with the same serotype, secondary infection with a different DV serotype can lead to increased risk of DHF and dengue shock syndrome (DSS). The DV genome consists of structural and non-structural proteins with DV serotypes 1-4 having approximately 60% 74% sequence homology in the E gene, which can induce cross-reacting antibodies.

Considerable effort has been devoted to the development of effective vaccines against DV. Live attenuated viruses, inactivated viruses, recombinant proteins, chimeric viruses, DNA vaccines, and synthetic peptides are being evaluated in the clinic. Due to the lack of an animal model or in vitro markers for attenuation in humans, chimeric vaccines with two or less dengue antigens, which results in limited T cell immunity, are being pursued. While antibodies against one serotype can be neutralizing and protective, risk of DHF after exposure to different serotypes has been observed. Early vaccine studies also demonstrated T cell responses to DV, but they were largely DV serotype specific. This may suggest that the level of presentation of MHC class I (MHCI) and class II (MHCII) antigens differs among serotypes. Beneficial effects of the vaccine-induced Th1 response further underscore the significance of the T cell response in vaccine development. The weight of evidence suggests that a useful Dengue virus vaccine will require both B- and T-cell responses to not only successfully protect against infection by each of the four serotypes, but also against the complications of antibody dependent enhancement (ADE).

The present disclosure involves peptides that are associated with the HLA-A2, HLA-A24, or HLA-B7 molecules, HLA-A2 supertypes, HLA-A24 supertypes, and HLA-B7 supertypes. A supertype is a group of HLA molecules that present at least one shared epitope. The present disclosure involves peptides that are associated with HLA molecules, and with the genes and proteins from which these peptides are derived.

Three different methodologies have typically been used for identifying the peptides that are recognized by CTLs in infectious disease field. These are: (1) the genetic method; (2) motif analysis: (3) the immunological and analytical chemistry methods or the Immunoproteomics method.

The genetic method is an approach in which progressively smaller subsets of cDNA libraries from diseased cells are transfected into cells that express the appropriate MHC molecule but not the disease-specific epitope. The molecular clones encoding T cell epitopes are identified by their ability to reconstitute disease specific T cell recognition of transfected cells. The exact T cell epitope is then identified by a combination of molecular subcloning and the use of synthetic peptides based on the predicted amino acid sequence. Such methods, however, are susceptible to inadvertent identification of cross-reacting peptides, and are not capable of identifying important post-translational modifications.

Motif analysis involves scanning a protein for peptides containing known class I MHC binding motifs, followed by synthesis and assay of the predicted peptides for their ability to be recognized by disease-specific CTL. This approach requires prior knowledge of the protein from which the peptides are derived and widely used in virus or bacterial infection field. This approach is also greatly hampered by the fact that not all of the predicted peptide epitopes are presented on the surface of a cell (Yewdell, J. W. and Bennink, J. R., Ann. Rev. Immunol., 17:51-88, (1999)), thus additional extensive experimentation is required to determine which of the predicted epitopes is useful.

Immunoproteomics method involves a combination of cellular immunology and mass spectrometry. This approach involves the actual identification of endogenous CTL epitopes present on the cell surface by sequencing the naturally occurring peptides associated with class I MHC molecules. In this approach, cells are first lysed in a detergent solution, the peptides associated with the class I MHC molecules are purified, and the peptides are fractionated by high performance liquid chromatography (HPLC). Peptide sequencing is readily performed by tandem mass spectrometry (Henderson, R. A. et al., Proc. Natl. Acad. Sci. U.S.A, 90:10275-10279, (1993).

A number of recent reports for different types of virus infections provide evidence that CTL specific for epitopes that are naturally processed and presented by infected cells have markedly greater impact on the control of virus replication. Undoubtedly, CTLs have been shown to play an important role in the elimination of dengue virus-infected cells. Thus, identification of antigenic peptides that are presented by infected cells and recognized by epitope-specific CTLs may suggest new ways to suppress viral replication and prevent persistent infection. Multiple peptides from conserved regions of dengue virus may prove essential in the development of a universally immunogenic vaccine. In recent years, several MHC class I specific peptides have been reported by the screening of algorithm-predicted T-cell epitopes using T cells from individuals participating in experimental DV vaccine trials as well as those infected with DV. However, these peptides were not subsequently investigated nor determined to be presented by DV infected cells.

Little is known about cross serotype conserved T cell epitopes that are immunologically relevant in eliciting an effective T cell response to the four DV serotypes. Several groups have attempted to identify T cell epitopes by either motif prediction of MHC binding peptides from Dengue proteins, or by screening overlapping peptides from structural and nonstructural Dengue proteins. Screening PBMCs from individuals in a DV vaccine trial and DV-infected patients using a panel of algorithm-derived peptide sequences identified a few DV serotype specific T cell epitopes. However, a comprehensive analysis of naturally presented epitopes on infected cells has never been undertaken or reported.

SUMMARY OF THE INVENTION

The present invention relates to immunogens comprising polypeptides with amino acid sequences comprising epitopic sequences selected from the sequences of SEQ ID NO: 1-17 and which immunogens facilitate a cytotoxic T lymphocyte (CTL)-mediated immune response against various serotype specific dengue virus (DV) infection. The present invention also relates to nucleic acid molecules that encode for the polypeptides their isoforms and splice variants from which the polypeptides are derived, of such immunogens, and which can also be used to facilitate an immune response against DV.

The present invention provides compositions comprising the immunogen described herein, and polynucleotides that direct the synthesis of such polypeptides, whereby the oligopeptides and polypeptides of such immunogens are capable of inducing a CTL response against cells expressing a protein comprising an epitopic sequence of at least one of SEQ ID NO: 1-17. The cells are usually DV infected cells, preferably dengue virus serotypes 1-4 expressing such proteins.

The present invention further relates to polynucleotides comprising the gene coding for a polypeptide of the immunogens disclosed herein. The present invention also provides methods that comprise contacting a lymphocyte, especially a CTL, with an immunogen or its isoforms or splice variants of the invention under conditions that induce a CTL response against a DV infected cell. The methods may involve contacting the CTL with the immunogenic peptide in vivo, in which case the peptides, polypeptides, and polynucleotides of the invention are used as vaccines, and will be delivered as a pharmaceutical composition comprising a pharmaceutically acceptable carrier or delivery system and the immunogen, typically along with an adjuvant or one or more cytokines.

Alternatively, the immunogens of the present invention can be used to induce a CTL response in vitro. The generated CTL can then be introduced into a patient with DV infection, more specifically DV serotypes 1-4. Alternatively, the ability to generate CTL in vitro could serve as a diagnostic for DV infection generally, including dengue virus serotypes 1-4.

BRIEF DESCRIPTION OF THE DRAWINGS

FIG. 2: Validation of naturally processed MHC class I peptides isolated from dengue virus infected DC/JY cells. MS/MS spectra of identified MHC peptides (Seq ID: 1-[P4], 2-[P2], 3-[P3], 15-[P1]) [P1A-P4A] and their synthetic analogs [P1B-P4B].

DETAILED DESCRIPTION OF THE INVENTION

Definitions

Figure 1:
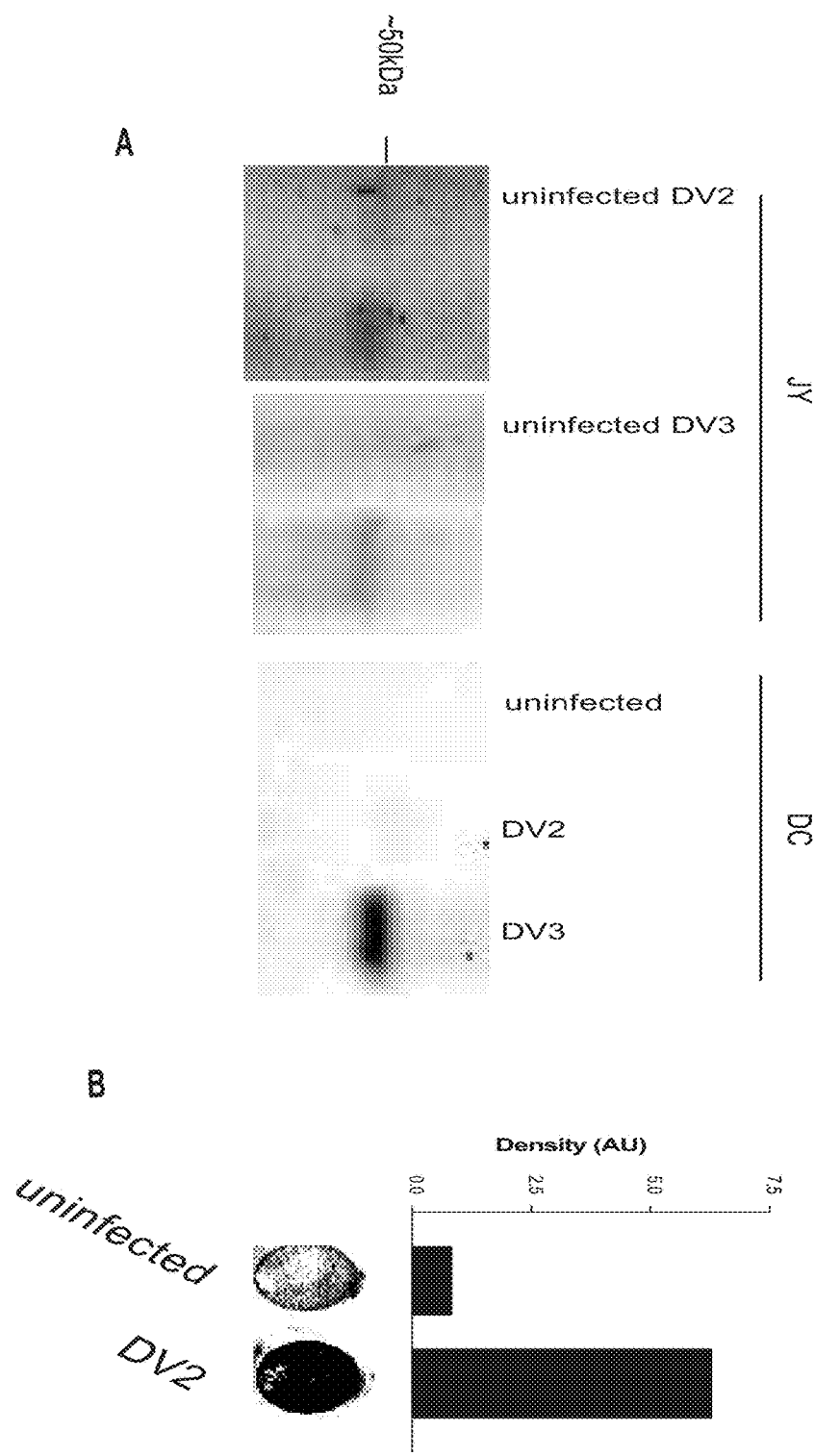
FIG. 1: Dengue virus infection analysis. (A) JY, HepG2 cells as well as DC from healthy HLA-A2+ donors were infected with DV2 and DV3 virus and incubated for 72 hrs. Cells were lysed and immunoblotted for E protein. (B) HepG2 cells infected with DV2 virus. After 72 hr incubation, cells were stained for E protein. Densitometry in arbitrary units (AU) using Odyssey Infrared Imaging System software.

As used herein and except as noted otherwise, all terms are defined as given below. The term "peptide" is used herein to designate a series of amino acid residues, connected one to the other typically by peptide bonds between the alpha-amino and carbonyl groups of the adjacent amino acids. The peptides are typically 9 amino acids in length, but can be as short as 8 amino acids in length, and as long as 14 amino acids in length. The series of amino acids are consider an "oligopeptide" when the amino acid length is greater than about 14 amino acids in length, typically up to about 30 to 40 residues in length. When the amino acid residue length exceeds 40 amino acid residues, the series of amino acid residues is termed "polypeptide".

A peptide, oligopeptide, polypeptide, protein, or polynucleotide coding for such a molecule is "immunogenic" and thus an immunogen within the present invention if it is capable of inducing an immune response. In the present invention, immunogenicity is more specifically defined as the ability to induce a CTL-mediated response. Thus, an immunogen would be a molecule that is capable of inducing an immune response, and in the present invention, a molecule capable of inducing a CTL response. An immunogen may have one or more isoforms or splice variants that have equivalent biological and immunological activity, and are thus also considered for the purposes of this invention to be immunogenic equivalents of the original, natural polypeptide.

A T cell "epitope" is a short peptide molecule that binds to a class I or II MHC molecule and that is subsequently recognized by a T cell. T cell epitopes that bind to class I MHC molecules are typically 8-14 amino acids in length, and most typically 9 amino acids in length.

Three different genetic loci encode for class I MHC molecules: HLA-A, HLA-B, and HLA-C. The present invention involves peptides that are associated with HLA-A2 supertypes. A supertype is a group of HLA molecules that present at least one shared epitope. MHC molecule peptides that have been found to bind to one member of the MHC allele supertype family (A2 for example) are thought to be likely to bind to other members of the same supertype family (A68 for example).

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence.

The term "nucleotide sequence" refers to a heteropolymer of deoxyribonucleotides. The nucleotide sequence encoding for a particular peptide, oligopeptide, or polypeptide naturally occurring or synthetically constructed.

The term "fragment," when referring to a coding sequence, means a portion of DNA comprising less than the complete coding region whose expression product retains essentially the same biological or immunological function or activity as the expression product of the complete coding region.

The term "isolated" means that the material is removed from its original environment (e.g., the natural environment if it is naturally occurring).

The polynucleotides, and recombinant or immunogenic polypeptides, disclosed in accordance with the present invention may also be in "purified" form.

The term "active fragment" means a fragment that generates an immune response (i.e., has immunogenic activity) when administered, alone or optionally with a suitable adjuvant, to an animal, such as a mammal, for example, a human, such immune response taking the form of stimulating a CTL response within the recipient. Alternatively, the "active fragment" may also be used to induce a CTL response in vitro.

As used herein, the terms "portion," "segment," and "fragment." when used in relation to polypeptides, refer to a continuous sequence of residues, such as amino acid residues, which sequence forms a subset of a larger sequence. For example, if a polypeptide were subjected to treatment with any of the common endopeptidases, the oligopeptides resulting from such treatment would represent portions, segments or fragments of the starting polypeptide.

The term "percent identity" when referring to a sequence, means that a sequence is compared to a described sequence after alignment of the sequence to be compared with the described sequence. The Percent Identity is determined according to the following formula:

Percent Identity=100[1−(C/R)]

wherein C is the number of differences between the Reference Sequence ("R") and the Compared Sequence ("C") over the length of alignment between R and C wherein (i) each base or amino acid in R that does not have a corresponding aligned base or amino acid in the C and (ii) each gap in R and (iii) each aligned base or amino acid in R that is different from an aligned base or amino acid in C, constitutes a difference; and R is the number of bases or amino acids over the length of the alignment with C with any gap created in R also being counted as a base or amino acid.

DESCRIPTION

The present invention embodies generally immunogens and immunogenic compositions, and methods of use thereof, for the prevention, treatment, and diagnosis of dengue virus infection, including DV serotypes 1-4. The immunogens comprise proteins or polypeptides whose amino acid sequences includes one or more epitopic oligopeptides with sequences selected from the group SEQ ID NO: 1-17. In addition, the invention further embodies polynucleotides that can be used to stimulate a CTL response against DV infection, and more specifically serotypes DV 1-4.

One embodiment of the present invention includes compositions for DV peptides, subsequence and portions thereof, nucleic acid sequences encoding DV peptides, subsequences and portions thereof, and host cells expressing DV peptides, subsequences and portions thereof. One particular aspect of the subsequence or portion of the DV polypeptide sequence includes epitopic peptides. These embodiments further incorporate useful pharmaceutical compositions such as, but not limited to, an adjuvant (e.g., Freund's complete or incomplete adjuvant) or administration with traditional prophylactic viral vaccine formulations (e.g., live attenuated viruses, inactivated viruses, recombinant proteins, chimeric viruses, DNA vaccines, and synthetic peptides).

The invention includes kits that contain DV peptides, subsequences and portions thereof, compositions, that optionally include instructions for treating (prophylactic or therapeutic), vaccinating or immunizing a subject against a DV infection, or treating (prophylactic or therapeutic) a subject having or at risk of having a Dengue virus infection or pathology.

In accordance with further embodiments of the invention, methods for treating a subject having a DV infection (acute) are provided. In one embodiment, a method includes administering to a subject in need thereof an amount of a DV peptide or epitopic peptide, subsequence or portion thereof, sufficient to treat the subject for the pathogen infection.

In accordance with further embodiments of the invention, there are provided prophylactic methods including methods of vaccinating and immunizing a subject against a DV infection (acute) such as, but not limited to, protecting a subject against a DV infection to decrease or reduce the probability of a DV infection or pathology in a subject or to decrease or reduce susceptibility of a subject to a DV infection or pathology or to inhibit or prevent a DV infection in a subject.

In accordance with further embodiments of the present invention specific oligopeptide sequences are disclosed with amino acid sequences shown in SEQ ID NO: 1-17 representing epitopic peptides (i.e. immunogenic oligopeptide sequences) of at least about 8 amino acids in length, preferably about 9 amino acids in length (i.e., nonapeptides), and no longer than about 14 amino acids in length and present as part of a larger structure, such as a polypeptide or full length protein.

The polypeptides forming the immunogens of the present invention have amino acid sequences that comprise at least one stretch, possibly two, or more stretches of about 8 to 10 or up to 14 residues in length and which stretches differ in amino acid sequence from the sequences of SEQ ID NO: 1-17 by no more than about 1 amino acid residue, preferably a conservative amino acid residue, especially amino acids of the same general chemical character, such as where they are hydrophobic amino acids.

These polypeptides are of any desired length so long as they have immunogenic activity in that they are able, under a given set of desirable conditions, to elicit in vitro or in vivo the activation of cytotoxic T lymphocytes (CTLs) (i.e., a CTL response) against a presentation of DV specific protein, especially DV 1-4 specific protein where said proteins are presented in vitro or in vivo by an antigen presenting cell (APC). The proteins and polypeptides forming the immunogens of the present invention can be naturally occurring or synthesized chemically.

The present invention further embodies an isolated polypeptide, especially one having immunogenic activity, the sequence of which comprises within it one or more stretches comprising any 2 or more of the sequences of SEQ ID NO: 1-17 and in any relative quantities and wherein said sequences may differ by one amino acid residues from the sequences of SEQ ID NO: 1-17 in any given stretch of 8 to 10, or up to 14 amino acid residues. Thus within the present invention, by way of a non-limiting example only, such polypeptide may contain as part of its amino acid sequence, nonapeptide fragments having up to 8 amino acids identical to a sequence of SEQ ID NO: 1, 2, 7, 8 such that the polypeptide comprises, in a specific embodiment, 2 segments with at least 8 residues identical to SEQ ID NO: 1 and SEQ ID NO: 2 and one segment with at least 8 residues identical to SEQ ID NO: 7. In other embodiments, other combinations and permutations of the epitopic sequences disclosed herein may be part of an immunogen of the present invention or of such a polypeptide so long as any such polypeptide comprises at least 2 such epitopes, whether such epitopes are different or the same.

All of the epitopic peptides of SEQ ID NO: 1 through 17 are derived from proteins expressed by DV infected cells and sequences and were identified through the method of Immunoproteomics and Automated High Through-put Sequencing (HTPS).

In addition to the sequences of SEQ ID NO: 1-17, the proteins and polypeptides forming the immunogens of the present invention further comprise one or more other immunogenic amino acid stretches known to be associated with DV infection, and more specifically DV serotypes 1-4, and which may stimulate a CTL response whereby the immunogenic peptides associate with HLA-A2 or HLA-A24 or HLA-B7, HLA supertypes, or any class 1 MHC (i.e., MHC-1) molecule.

The immunogens of the present invention can be in the form of a composition of one or more of the different immunogens and wherein each immunogen is present in any desired relative abundance.

The oligopeptides and polypeptides useful in practicing the present invention may be derived by fractionation of naturally occurring proteins by methods such as protease treatment, or they may be produced by recombinant or synthetic methodologies that are well known and clear to the skilled artisan. The polypeptide may comprise a recombinant or synthetic polypeptide having at least one of SEQ ID NO: 1-17. Thus, oligopeptides and polypeptides of the present invention have at least one immunogenic peptides within the amino acid sequence of said oligopeptides and polypeptides, and said immunogenic peptides, or epitopes, which are the same or different, or may have any number of such sequences wherein some of them are identical to each other in amino acid sequence and said epitopic sequences occur in any order within said immunogenic polypeptide sequence. The location of such sequences within the sequence of a polypeptide forming an immunogen may affect relative immunogenic activity. In addition, immunogens of the present invention may comprise more than one protein comprising the amino acid sequences disclosed herein. Such polypeptides may be part of a single composition or may themselves be covalently or non-covalently linked to each other.

The immunogenic peptides disclosed herein may also be linked directly to, or through a spacer or linker to: an immunogenic carrier such as serum albumin, tetanus toxoid, keyhole limpet hemocyanin, dextran, or a recombinant virus particle; an immunogenic peptide known to stimulate a T helper cell type immune response; a cytokine such as interferon gamma or GMCSF; a targeting agent such as an antibody or receptor ligand; a stabilizing agent such as a lipid; or a conjugate of a plurality of epitopes to a branched lysine core structure, such as the so-called "multiple antigenic peptide" described in (Posneft, D. N. et al., J. Biol. Chem., 263:1719-1725, (1988)); a compound such as polyethylene glycol to increase the half-life of the peptide; or additional amino acids such as a leader or secretory sequence, or a sequence employed for the purification of the mature sequence. Spacers and linkers typically comprise relatively small, neutral molecules. In addition, such linkers need not be composed of amino acids but any oligomeric structures will do as well so long as they provide the correct spacing so as to optimize the desired level of immunogenic activity of the immunogens of the present invention. The immunogen may therefore take any form that is capable of eliciting a CTL response.

Immunogens, such as proteins, oligopeptides and polypeptides of the invention, are structures that contain the peptides disclosed according to the present invention but such immunogenic peptides may not necessarily be attached thereto by the conventional means of using ordinary peptide bounds. The immunogens of the present invention simply contain such peptides as part of their makeup, but how such peptides are to be combined to form the final immunogen is through any means known in the art.

The peptides that are naturally processed and bound to a class I MHC molecule, and which are recognized by the DV-specific CTL, need not be the optimal peptides for stimulating a CTL response. Thus, the ability to modify a peptide such that it more readily induces a CTL response is considered. Generally, the peptides may be modified at amino acid residues that are predicted to interact with the class I MHC molecule, in which case the goal is to create a peptide that has a higher affinity for the class I MHC molecule than does the original peptide. The peptides can be modified at amino acid residues that are predicted to interact with the T cell receptor on the CTL, in which case the goal is to create a peptide that has a higher affinity for the T cell receptor than does the original peptide. Both of these types of modifications can result in a variant peptide that is related to an original peptide, but which is better able to induce a CTL response than is the original peptide as selected from SEQ ID NO: 1-17.

The original peptides disclosed herein can be further modified by the substitution of one or more residues at different, possibly selective, sites within the peptide chain. Such substitutions can be conservative. Less conservative substitutions or even highly non-conservative replacements are also considered since chemical effects are not totally predictable.

Based on cytotoxicity assays, an epitope is considered substantially identical to the reference peptide if it has at least 10% of the antigenic activity of the reference peptide as defined by the ability of the substituted peptide to reconstitute the epitope recognized by a CTL in comparison to the reference peptide. Thus, when comparing the lytic activity in the linear portion of the effector:target curves with equimolar concentrations of the reference and substituted peptides, the observed percent specific killing of the target cells incubated with the substituted peptide should be equal to that of the reference peptide at an effector:target ratio that is no greater than 10-fold above the reference peptide effector:target ratio at which the comparison is being made.

Preferably, when the CTLs specific for a peptide of SEQ ID NO: 1-17 are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 µM, and most preferably no more than about 10 pM. It is also preferred that the substituted peptide be recognized by CTLs from at least two or more individuals, preferably three.

Thus, the epitopes of the present invention may be identical to naturally occurring DV infected cell-associated or DV-specific epitopes or may include epitopes that differ by no more than 4 residues from the reference peptide, as long as they have substantially identical antigenic activity.

It should be appreciated that an immunogen may comprise one or more peptides from SEQ ID NO: 1-17, a plurality of peptides selected from SEQ ID NO: 1-17, or comprise a polypeptide that itself comprises one or more of the epitopic peptides of SEQ ID NO: 1-17.

The immunogenic peptides and polypeptides of the invention can be prepared synthetically, or any means known in the art, including those techniques involving recombinant DNA technology.

The coding sequences for peptides of the length contemplated herein can be synthesized on commercially available automated DNA synthesizers or modified to a desired amino acid substitution. The coding sequence can be transformed or transfected into suitable hosts to produce the desired fusion protein.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. Such cells can routinely be utilized for assaying CTL activity by having said genetically engineered, or recombinant, host cells express the immunogenic peptides of the present invention.

The immunogenic peptides of the present invention may be used to elicit CTLs ex vivo from either healthy individuals or from DV infected individuals. Such responses are induced by incubating in tissue culture the individual's CTL precursor lymphocytes together with a source of antigen presenting cells and the appropriate immunogenic peptide. The CTLs generated with peptides and polypeptides of the invention can be prepared by any means known in the art, including those techniques involving ex vivo adoptive cell therapy technologies.

A variety of approaches are known in the art that allow polynucleotides to be introduced and expressed in a cell, thus providing one or more peptides of the invention to the class I MHC molecule binding pathway. Oligonucleotides that code for one or more of the peptides of the invention can be provided to antigen presenting cells in such a fashion that the peptides associate with class 1 MHC molecules and are presented on the surface of the antigen presenting cell, and consequently are available to stimulate a CTL response.

By preparing the stimulator cells used to generate an in vitro CTL response in different ways, it is possible to control the peptide specificity of CTL response. For example, the CTLs generated with a particular peptide will necessarily be specific for that peptide. Likewise, CTLs that are generated with a polypeptide or polynucleotide expressing or coding for particular peptides will be limited to specificities that recognize those peptides. More broadly, stimulator cells, and more specifically dendritic cells, can be incubated in the presence of the whole parent protein. As a further alternative, stimulator cells, and more specifically dendritic cells, can be transduced or transfected with RNA or DNA comprising the polynucleotide sequence encoding the protein. Under these alternative conditions, peptide epitopes that are naturally cleaved out of the protein, and which are generated in addition to peptide epitopes of SEQ ID NO:1-17 can associate with an appropriate class I MHC molecule, which may or may not include HLA-A1, -A2, -A24, -B7. The selection of antigen presenting cells and the type of antigen with which to stimulate the CTL, is left to the ordinary skilled artisan.

In certain embodiments, the methods of the present invention include a method for inducing a CTL response in vitro that is specific for DV infected cell expressing a molecule from A1, A2, A24, or B7 supertypes, whereby the method comprises contacting a CTL precursor lymphocyte with an antigen presenting cell that has bound an immunogen or has exogenously acquired an immunogenic oligopeptide or polypeptide comprising one or more of the peptides disclosed according to the invention.

Another embodiment is directed to a process for inducing a CTL response in vitro that is specific for DV infected cell expressing a molecule from A1, A2, A24, or B7 supertypes, comprising contacting a CTL precursor lymphocyte with an antigen presenting cell that is expressing a polynucleotide coding for a polypeptide of the invention and wherein said polynucleotide is operably linked to a promoter.

A variety of techniques exist for assaying the activity of CTL. Such assays are well-known in the art and their selection is left to the skilled artisan. CTLs are known to release, induce, increase, enhance, stimulate or activate expression or production of a cytokine. Assay selection is left to the skilled artisan.

After expansion of the antigen-specific CTLs, the CTLs are then adoptively transferred back into the patient, where they will destroy their specific target cell. Methodologies for reinfusing T cells into a patient are well known and exemplified in U.S. Pat. No. 4,844,893 to Honski, et al., and U.S. Pat. No. 4,690,915 to Rosenberg.

The peptide-specific CTL can be purified from the stimulator cells prior to infusion into the patient. For example, monoclonal antibodies directed toward the cell surface protein CD8, present on CTL, can be used in conjunction with a variety of isolation techniques such as antibody panning, flow cytometric sorting, and magnetic bead separation to purify the peptide-specific CTL away from any remaining non-peptide specific lymphocytes or from the stimulator cells.

Thus, one embodiment of the present invention relates to a process for treating a subject with DV infection or DV exposure characterized by infected cells expressing complexes of a molecule from A2, or A24, or B7 supertypes, whereby CTLs produced in vitro according to the present invention are administered in an amount sufficient to destroy the infected cells through direct lysis or to effect the destruction of the infected cells indirectly through the elaboration of cytokines.

Another embodiment of the present invention is directed to a process for treating a subject with infection characterized by infected cells expressing any class I MHC molecule and an epitope of SEQ ID NO: 1-17, whereby the CTLs are produced in vitro and are specific for the epitope or original protein and are administered in an amount sufficient to destroy the infected cells through direct lysis or to effect the destruction of the infected cells indirectly through the elaboration of cytokines.

The ex vivo generated CTL can be used to identify and isolate the T cell receptor molecules specific for the peptide. The genes encoding the alpha and beta chains of the T cell receptor can be cloned into an expression vector system and transferred and expressed in naive T cells from peripheral blood, T cells from lymph nodes, or T lymphocyte progenitor cells from bone marrow. These T cells, which would then be expressing a peptide-specific T cell receptor, would then have anti-DV reactivity and could be used in adoptive therapy of DV infection, and more specifically DV serotypes 1-4.

In addition to their use for therapeutic or prophylactic purposes, the immunogenic peptides of the present invention are useful as screening and diagnostic agents. Thus, the immunogenic peptides of the present invention, together with modern techniques of CTL screening, make it possible to screen patients for the presence of T cells specific for these peptides as a test for DV infection, exposure and immune response. The results of such screening may help determine the efficacy of proceeding with the regimen of treatment disclosed herein using the immunogens of the present invention.

The oligopeptides of the invention, such as SEQ ID NO: 1-17, can also be used to prepare class I MHC tetramers or pentamers which can be used in conjunction with flow cytometry to quantitate the frequency of peptide-specific CTL that are present in a sample of lymphocytes from an individual. Specifically, for example, class I MHC molecules comprising peptides of SEQ ID NO: 1-17, would be combined to form tetramers as exemplified in U.S. Pat. No. 5,635,363. Said tetramers would find use in monitoring the frequency of CTLs in the peripheral blood or lymph nodes of an individual who is vaccinated or undergoing immunotherapy with the peptides, proteins, or polynucleotides of the invention, and it would be expected that successful immunization would lead to an increase in the frequency of the peptide-specific CTL.

Alternatively, the immunogenic peptides disclosed herein, as well as functionally similar homologs thereof, may be used to screen a sample for the presence of CTLs that specifically recognize the corresponding epitopes. The lymphocytes to be screened in this assay will normally be obtained from the peripheral blood, but lymphocytes can be obtained from other sources, including lymph nodes, spleen, and body fluids. The peptides of the present invention may then be used as a diagnostic tool to evaluate the efficacy of the immunotherapeutic treatments disclosed herein. Thus, the in vitro generation of CTL as described above would be used to determine if patients are likely to respond to the peptide in vivo. Similarly, the in vitro generation of CTL cam be done with samples of lymphocytes obtained from the patient before and after treatment with the peptides. Successful generation of CTL in vivo should then be recognized by a correspondingly easier ability to generate peptide-specific CTL in vitro from lymphocytes obtained following treatment in comparison to those obtained before treatment.

As stated above, a prophylactic or therapeutic vaccine in accordance with the present invention may include one or more of the hereinabove described polypeptides or active fragments thereof, or a composition, or pool, of immunogenic peptides disclosed herein. When employing more than one polypeptide or active fragment, such as two or more polypeptides and/or active fragments may be used as a physical mixture or as a fusion of two or more polypeptides or active fragments. The fusion fragment or fusion polypeptide may be produced, for example, by recombinant techniques or by the use of appropriate linkers for fusing previously prepared polypeptides or active fragments.

The immunogenic molecules of the invention, including vaccine compositions, may be utilized according to the present invention for purposes of preventing, suppressing or treating diseases causing the expression of the immunogenic peptides disclosed herein, such as where the antigen is being expressed by DV infected cells. As used in accordance with the present invention, the term "prevention" relates to a process of prophylaxis in which an animal, especially a mammal, and most especially a human, is exposed to an immunogen of the present invention prior to the induction or onset of the disease process. This could be done where an individual is at high risk for DV infection based on the living or travel to the DV endemic areas. Alternatively, the immunogen could be administered to the general population as is frequently done for any infectious diseases. Alternatively, the term "suppression" is often used to describe a condition wherein the disease process has already begun but obvious symptoms of said condition have yet to be realized. Thus, the cells of an individual may have been infected but no outside signs of the disease have yet been clinically recognized. In either case, the term prophylaxis can be applied to encompass both prevention and suppression. Conversely, the term "treatment" is often utilized to mean the clinical application of agents to combat an already existing condition whose clinical presentation has already been realized in a patient. This would occur where an individual has already been diagnosed as having confirmed DV infection.

It is understood that the suitable dosage of an immunogen of the present invention will depend upon the age, sex, health, and weight of the recipient, the kind of concurrent treatment, if any, the frequency of treatment, and the nature of the effect desired. However, the most preferred dosage can be tailored to the individual subject, as determined by the researcher or clinician. The total dose required for any given treatment will commonly be determined with respect to a standard reference dose as set by a manufacturer, such as is commonly done with vaccines, such dose being administered either in a single treatment or in a series of doses, the success of which will depend on the production of a desired immunological result (i.e., successful production of a CTL-mediated response to the antigen, which response gives rise to the prevention and/or treatment desired).

The therapeutically effective amount of a composition containing one or more of the immunogens of this invention, is an amount sufficient to induce an effective CTL response to prevent, cure or arrest disease progression. Thus, this dose will depend, among other things, on the identity of the immunogens used, the nature of the disease condition, the severity of the disease condition, the extent of any need to prevent such a condition where it has not already been detected, the manner of administration dictated by the situation requiring such administration, the weight and state of health of the individual receiving such administration, and the sound judgment of the clinician or researcher. Thus, for purposes of prophylactic or therapeutic administration, effective amounts would generally lie within the range of from 1.0 μg to about 5,000 μg of peptide for a 70 kg patient, followed by boosting dosages of from about 1.0 μg to about 1,000 μg of peptide pursuant to a boosting regimen over days, weeks or months, depending on the recipient's response and as necessitated by subsequent monitoring of CTL-mediated activity within the bloodstream. Of course, such dosages are to be considered only a general guide and, in a given situation, may greatly exceed such suggested dosage regimens where the clinician believes that the recipient's condition warrants more aggressive administration schedule. The efficacy of administering additional doses, and of increasing or decreasing the interval, may be re-evaluated on a continuing basis, in view of the recipient's immunocompetence (for example, the level of CTL activity with respect to acute or chronic DV infection).

For such purposes, the immunogenic compositions according to the present invention may be used against a DV infection by administration to an individual by a variety of routes. The composition may be administered parenterally or orally, and, if parenterally, either systemically or topically. Parenteral routes include subcutaneous, intravenous, intradermal, intramuscular, intraperitoneal, intranasal, transdermal, or buccal routes. One or more such routes may be employed. Parenteral administration can be, for example, by bolus injection or by gradual perfusion over time.

Generally, vaccines are prepared as injectables, in the form of aqueous solutions or suspensions. Pharmaceutical carriers, diluents and excipients can be generally added that are compatible with the active ingredients and acceptable for pharmaceutical use.

The concentration of the CTL stimulatory peptides of the invention in pharmaceutical formulations are subject to wide variation, including anywhere from less than 0.01% by weight to as much as 50% or more. Factors such as volume and viscosity of the resulting composition must also be considered. The solvents, or diluents, used for such compositions include water, dimethylsulfoxide, PBS (phosphate buffered saline), or saline itself, or other possible carriers or excipients.

Aerosol administration is also an alternative, requiring only that the immunogens be properly dispersed within the aerosol propellant. The use of a surfactant to properly disperse the immunogen may be required. Representative surfactants include caproic, octanoic, lauric, palmitic, stearic, linoleic, linolenic, olesteric and oleic acids with an aliphatic polyhydric alcohol or its cyclic anhydride. The surfactant may constitute 0.1-20% by weight of the composition, preferably 0.25-5%.

The peptides and polypeptides of the invention may also be delivered with an adjuvant. Adjuvant effects can also be obtained by injecting a variety of cytokines along with the immunogens of the invention.

The peptides and polypeptides of the invention can also be added to professional antigen presenting cells such as dendritic cells that have been prepared ex vivo.

The present invention is also directed to a vaccine in which an immunogen of the present invention is delivered or administered in the form of a polynucleotide encoding a polypeptide or active fragment as disclosed herein, whereby the peptide or polypeptide or active fragment is produced in vivo. The polynucleotide may be included in a suitable expression vector and combined with a pharmaceutically acceptable carrier. A wide variety of vectors are available and apparent to those skilled in the art. Vaccinia vectors and methods useful in immunization protocols are described in U.S. Pat. No. 4,722,848, the disclosure of which is incorporated herein by reference in its entirety.

Regardless of the nature of the composition given, additional vaccine compositions may also accompany the immunogens of the present invention. Thus, for purposes of preventing or treating DV infection (e.g., prophylactic or therapeutic vaccine), compositions containing the immunogens disclosed herein may, in addition, contain other vaccine pharmaceuticals. The use of such compositions with multiple active ingredients is left to the discretion of the clinician.

While examples are provided to illustrate the invention, it is to be understood that these examples in no way limit the invention to the embodiments described herein and that other embodiments and uses will no doubt suggest themselves to those skilled in the art. All publications, patents, and patent applications cited herein are hereby incorporated by reference, as are the references cited therein. It is also to be understood that throughout this disclosure where the singular is used, the plural may be inferred and vice versa and use of either is not to be considered limiting.

Example

Dengue virus serotype 2 (DV2) (strain-16681), as well as DV type 3 (DV3) (strain-16562), were propagated in Vero cells and collected at 4 days post infection (dpi). Titer was determined using a plaque assay in Vero cells. Thai isolates of all four DV serotypes were propagated. All infections were carried out at five MOI for 1 hr, after which, virus was removed and cells were incubated for additional 48-72 hrs.

HepG2, hepatoma cells, JY, EBV transformed lymphoblastoid B cells, T2, lymphoblasts, and K562, human leukemia cells were obtained from ATCC. HepG2 were maintained in DMEM:F12 medium while JY, T2, and K562 were maintained in RPMI 1640 (Mediatech. Manassas, Va.) supplemented with 10% fetal bovine serum, and maintained at 37° C. in a humidified incubator with 5% CO2.

Dendritic cells (DC) were generated from leukopheresis obtained from HLA-A2+ healthy donors (Research Blood Components, LLC, Brighton, Mass.).

Cell lysates from uninfected and Dengue-infected cell lines were tested for dengue E protein expression by western blot analysis. Infected cells were also analyzed for Dengue virus E protein using standard immunohistochemical methods.

JY cells and DCs were infected with DV2 and DV3 respectively at five MOI. After a 1 hr pulse, virus was washed away, and cells were incubated for 72 hrs at 37° C. before harvested and processed for MHC peptide analysis.

Cell lysates were prepared from dengue infected cells and MHC/peptide complexes were isolated by immunoaffinity chromatography using MHC molecule specific antibodies The peptides purified from the MHC molecules were fractionated using C-18 reversed phase (RP) column (4.6 mm diameter×150 mm length) using an offline HPLC (Dionex, Sunnyvale, Calif.). The peptide containing fractions were collected and dried to 6 μL under vacuum for LC/MS/MS analysis.

Mass spectrometry experiments were carried out using LTQ (Thermo) and Orbitrap instruments interfaced with nano ultimate HPLC (Dionex). RP-HPLC purified peptide fractions were injected individually into the LC-MS/MS system to identify the sequences of the peptides. The peptides were analyzed using a Data-Dependent method. The acquired spectra data were searched against Dengue (DV 1-4 serotypes) protein database using Proteome Discoverer (Thermo) to interpret data and derive peptide sequences.

Synthetic peptides were made and subjected to LC-MS/MS analysis under identical experimental conditions as described above and their sequences were confirmed based on their MS/MS data. Candidate peptide sequences were confirmed by comparison of their MS/MS spectra with that of their synthetic analogs.

Heparinized blood from healthy HLA-A2+ donors was purchased from Research Blood Components, LLC (Brighton, Mass.). Peripheral blood mononuclear cells (PBMC) were purified using differential centrifugation following standard methods. PBMC were used to generate peptide specific CTL as described previously (James S. Testa, et al. J Infect Dis 205(4): 647-655. (2012)).

Antigen stimulated interferon-γ (IFN-γ) release as a measure of CTL activation was assayed using an ELISPOT assay kit (BD-Pharmingen, San Jose, Calif.) according to the manufacturer's instructions. Results are presented as the number of interferon-γ producing cells per 1E6 PBMCs. Each assay was performed with PBMC from at least three different healthy HLA-A2+ donors. Error bars represent SEM of experimental replicates.

Seventeen epitopes including HLA-A2, A24, B7 and HLA-DR specific motifs were identified (Table 2) and four HLA-A2 specific epitopes (Seq ID: 1, 2, 3 and 15) were selected for CTL characterization. Synthetic peptides were made and used for CTL analysis. Table 2:

MHC Class I Associated T Cell Epitopes Presented by the Dengue Virus Infected Cells

| Seq ID | Peptide | Protein | Accession ID |
| --- | --- | --- | --- |
| 1 | NIQTAINQV | NS4B | Q9WDA6 |
| 2 | VTLLCLIPTV | Capsid C | Q2YHF2 |
| 3 | TITEEIAVQ | NS4B | P29990 |
| 4 | VLGWLEKYGV | NS5 | gi158851822 |
| 5 | ILGGLTWM | NS2A | gi148828521 |
| 6 | KILIGSVITW | Envelope glycoprotein | gi259157612 |
| 7 | LFLGFTVQADI | Envelope glycoprotein | gi28171600 |
| 8 | LFGKGGIVTR | Glycoprotein | gi1000739 |
| 9 | SPSRLASAI | NS1 | gi28171290 |
| 10 | IPSENEVKL | NS1 | gi224383594 |
| 11 | NIQVAINQV | NS4B | P33478 |
| 12 | NIQAAINQV | NS4B | P29990 |
| 13 | VTLYLGVMV | Capsid C | P27912 |
| 14 | VTLVLVGIV | Capsid C | P29991 |
| 15 | KLAEAIFKL | NS5 | P29990 |
| 16 | LMWKQVTPELNHILS | NS1 | gi28171290 |
| 17 | AGPLVAGGMLIACY | NS2B | gi239840450 |

Productive Infection with Dengue Virus Strains

We determined the infectivity of JY, HepG2 cells and primary human DCs from HLA-A*0201+ donors, which possess high levels of the MHC class I molecule that is most globally prevalent, HLA-A molecule. The cells were infected with DV2 and DV3, and expression of the envelope E protein was demonstrated (FIG. 1A). In addition, expression of E protein using an immunohistochemical method was demonstrated for HepG2 cells (FIG. 1B).

Identification of MHC Class I Presented Peptides by Nano-LC/MS/MS Analysis

MHC class I associated peptides isolated from dengue virus infected cells were subjected to LC/MS/MS analysis to identify the peptides and their corresponding proteins. Employing this strategy, we identified seventeen MHC associated peptides. Seq ID: 1-15 represents MHC class I peptide of HLA-A2, A24 and B7 supertypes and Seq ID: 16 &17 represents MHC class 11 specific peptides. Prior to CTL characterization experiments, we confirmed the authenticity of four HLA-A2 specific peptides (Seq ID: 1-[P4], 2-[P2], 3-[P3], 15-[P1]) using their synthetic peptide analogs. The results of validation experiments on these 4 peptides and their MS/MS spectra are shown in FIG. 2.

Figure 3:
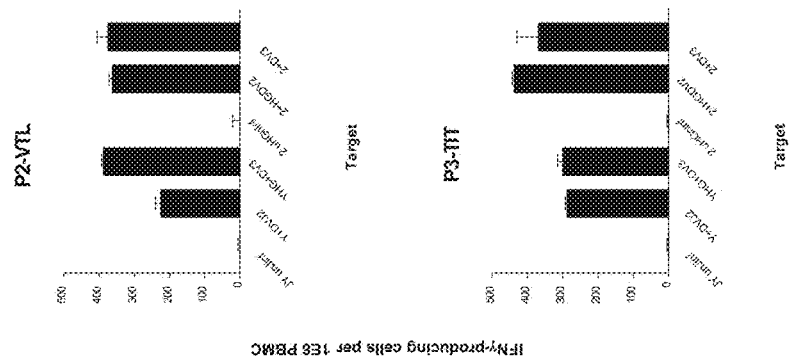
FIG. 3: CTL generated with DV epitopes are specific and cross-reactive. (A) T2 cells were pulsed with peptide and used as targets in an ELISpot assay with CTL that were generated from HLA-A2+ PBMCs against specific peptides. (B). JY and HepG2 cells were infected with either DV2 or DV3 and used as targets in an ELISpot assay. K562 were also used as NK cell target cells. Results were normalized against peptide unpulsed controls.
Figure 3:
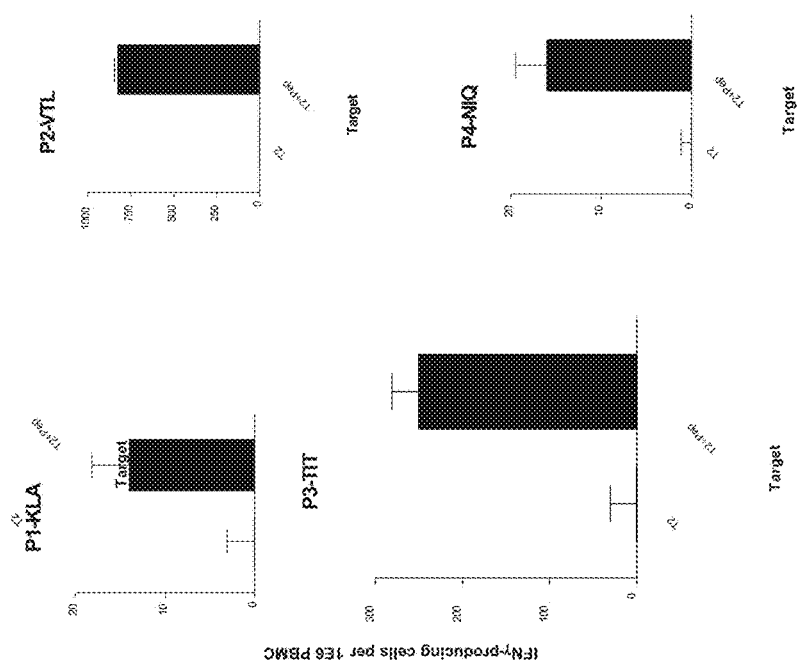

Cytotoxic T Cells Generated Against Dengue Virus Epitopes Recognize Peptide Loaded Targets as Well as DV-Infected Cells In order to characterize the functionality of the identified DV epitopes, we generated cytotoxic T cells from HLA-A2+ healthy donors using synthetic peptides corresponding to the identified epitopes. The cultures were tested in overnight ELISpot assays to measure IFNγ release from activated CTLs. As shown in FIG. 3A, CTLs generated against all 4 DV peptides recognize T2 cells loaded with the corresponding synthetic peptide. Next, to confirm CTL activation against DV-infected targets, JY and HepG2 cells were infected with both DV2 and DV3 virus and used as targets in CTL ELISpot assays. As expected, all DV-infected cells activated CTL to secrete IFNγ (FIG. 3B). In addition, K562 cells, a known NK cell target, were used as targets to measure non-specific IFNγ secretion.

Figure 4:
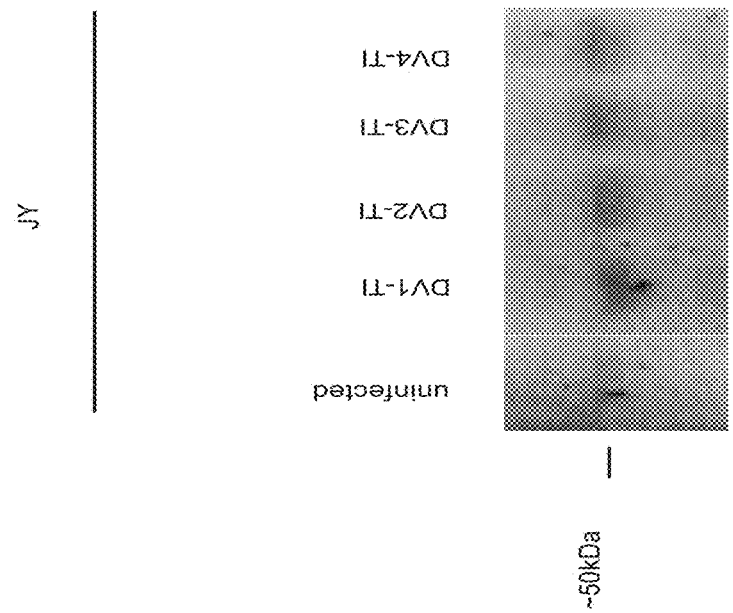
FIG. 4: CTL generated with DV epitopes cross-react with Thai isolates of DV. (A) HepG2 cells were infected with Thai isolates of DV and stained for E protein after 72 hr infection. Densitometry is in arbitrary units (AU), using Odyssey Infrared Imaging System software. (B) JY cells were infected with Thai isolates of DV. Following a 72 hr infection, cells were lysed and immunoblotted for E protein. Either HepG2 (C) or JY (D) were infected with DV Thai isolates and used as targets in an ELISpot assay. CTL were generated against P1-4 derived from DV-infected cells. Results were normalized against negative (uninfected) controls.
Figure 4:
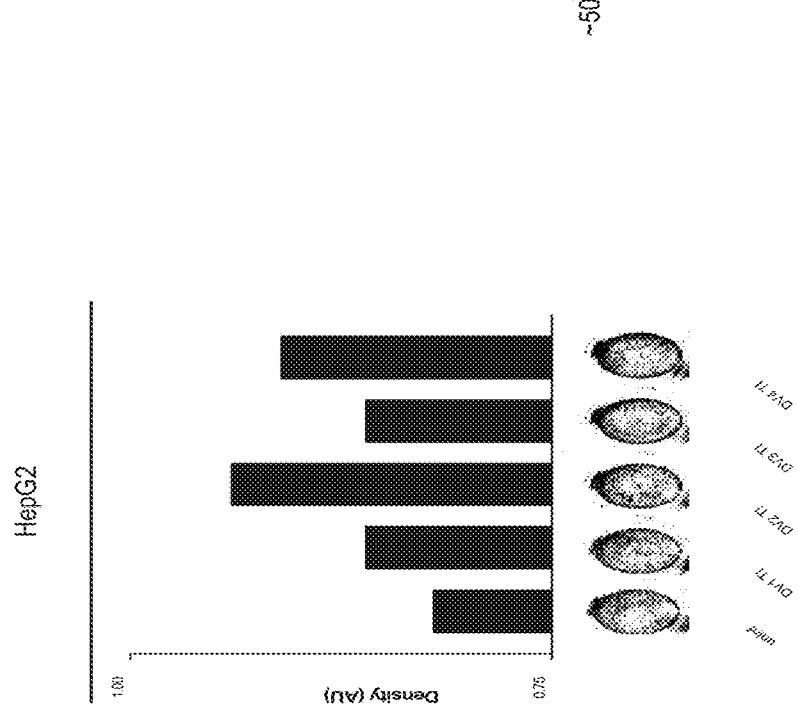

Epitope-Specific CTLs Generated from DV-Infected Cells Recognize Cells Infected with Thai DV Isolates We tested CTLs generated against the 4 epitopes using targets infected with all four DV serotypes. We infected HepG2 cells (FIG. 4A) or JY cells (FIG. 4B) with DV1-4 Thai isolates and verified protein expression. When infected HepG2 cells were used as targets in a CTL assay, all four epitope-specific CTLs were activated against all four serotypes, although not to the same degree (FIG. 4C). In addition to HepG2 cells, we also tested professional APC JY cells, as targets. As illustrated in FIG. 4D, most infected targets activate peptide-specific CTL. However, Seq ID 15 [P1] or Seq ID: 2 [P2] specific CTL recognized only DV2-infected targets.

Although the present invention has been described with reference to specific embodiments, workers skilled in the art will recognize that many variations may be made therefrom, for example in the particular experimental conditions herein described, and it is to be understood and appreciated that the disclosures in accordance with the invention show only some preferred embodiments and objects and advantages of the invention without departing from the broader scope and spirit of the invention. It is to be understood and appreciated that these discoveries in accordance with this invention are only those which are illustrated of the many additional potential applications that may be envisioned by one of ordinary skill in the art, and thus are not in any way intended to be limiting of the invention. Accordingly, other objects and advantages of the invention will be apparent to those skilled in the art from the detailed description together with the claims.

SEQUENCE LISTING

| Seq ID No | Peptide | Protein | Accession ID |
|---|---|---|---|
| Seq ID No 1 | NIQTAINQV | NS4B | Q9WDA6 |
| Seq ID No 2 | VTLLCLIPTV | Capsid C | Q2YHF2 |
| Seq ID No 3 | TITEEIAVQ | NS4B | P29990 |
| Seq ID No 4 | VLGWLEKYGV | NS5 | gi158851822 |
| Seq ID No 5 | ILGGLTWM | NS2A | gi148828521 |
| Seq ID No 6 | KILIGSVITW | Envelope glycoprotein | gi259157612 |
| Seq ID No 7 | LFLGFTVQADI | Envelope glycoprotein | gi28171600 |
| Seq ID No 8 | LFGKGGIVTR | Glycoprotein | gi1000739 |
| Seq ID No 9 | SPSRLASAI | NS1 | gi28171290 |
| Seq ID No 10 | IPSENEVKL | NS1 | gi224383594 |
| Seq ID No 11 | NIQVAINQV | NS4B | P33478 |
| Seq ID No 12 | NIQAAINQV | NS4B | P29990 |
| Seq ID No 13 | VTLYLGVMV | Capsid C | P27912 |
| Seq ID No 14 | VTLVLVGIV | Capsid C | P29991 |
| Seq ID No 15 | KLAEAIFKL | NS5 | P29990 |
| Seq ID No 16 | LMWKQVTPELNHILS | NS1 | gi28171290 |
| Seq ID No 17 | AGPLVAGGMLIACY | NS2B | gi239840450 |

I claim:

1. A method for inducing an immune response to dengue virus infection in a subject comprising administering an immunogenic composition comprising (i) a peptide consisting of the amino acid sequence of SEQ ID NO: 15 that binds to class I MHC molecules to induce a cytotoxic T lymphocyte-mediated immune response, or a variant thereof having an improved ability to bind to MHC class I molecules; and (ii) a peptide comprising the amino acid sequence of any one of SEQ ID NOs: 2, 3, 4, 5, 6, 7, 8, 9, 10, 11, 12, 14, 16 and 17 or consisting of the amino acid sequence of SEQ ID NOs: 1 or 13, or a variant thereof having an improved ability to bind to MHC class I molecules.

2. The method of claim 1, wherein the immunogenic composition further comprises a pharmaceutically acceptable carrier.

3. The method of claim 2 wherein the pharmaceutically acceptable carrier is an adjuvant.

4. The method of claim 1 wherein said immunogenic composition is a peptide, oligopeptide, or polypeptide containing said peptides of (i) and (ii).

5. The method of claim 4 wherein the peptide of (i) or (ii) is obtained from a fragmented and processed peptide, oligopeptide, or polypeptide.

6. The method of claim 1 wherein the variant differs by no more than at least one amino acid from the amino acid sequence from which it varies.

7. The method of claim 6 where the one amino acid difference is a conservative amino acid substitution.

8. The method of claim 6 where the amino acid difference is a substitution of one hydrophobic amino acid with another hydrophobic amino acid.

9. The method of claim 1 wherein said cytotoxic T lymphocyte-mediated immune response is against at least one serotype specific dengue virus infection.

10. The method of claim 9 wherein said cytotoxic T lymphocyte-mediated immune response is against serotype specific dengue virus infections from a group consisting of serotype 1, 2, 3, 4, and combinations thereof.

11. The method of claim 10 wherein said cytotoxic T lymphocyte-mediated immune response is against serotypes 1, 2, 3, and 4.

12. A method for inducing a cytotoxic T lymphocyte-mediated immune response in a subject comprising administering an effective amount of a composition comprising (i) a peptide consisting of the amino acid sequence of SEQ ID NO: 15 or a variant thereof having an improved ability to bind to MHC class I molecules and (ii) a peptide comprising the amino acid sequence of any one of SEQ ID NOs: 2, 3, 4, 5, 6, 7, 8, 9, 10, 11, 12, 14, 16 and 17 or consisting of the amino acid sequence of SEQ ID NOs: 1 or 13, or a variant thereof having an improved ability to bind to MHC class I molecules.

13. The method of claim 12 wherein said composition is a peptide, oligopeptide, or polypeptide containing said peptides of (i) and (ii).

14. The method of claim 13 wherein the peptide of (i) or (ii) is obtained from a fragmented and processed peptide, oligopeptide, or polypeptide.

15. The method of claim 12 wherein the variant differs by no more than one amino acid from the amino acid sequence form which it varies.

16. The method of claim 15 where the one amino acid difference is a conservative amino acid substitution.

17. The method of claim 15 where the amino acid difference is a substitution of one hydrophobic amino acid with another hydrophobic amino acid.

18. A method of preventing disease caused by dengue virus in a subject comprising administering to the subject an effective amount of a vaccine comprising (i) a peptide consisting of SEQ ID NO: 15 and (ii) a peptide comprising the amino acid sequence of any one of SEQ ID NOs: 2, 3, 4, 5, 6, 7, 8, 9, 10, 11, 12, 14, 16 and 17 or consisting of the amino acid sequence of SEQ ID NOs: 1 or 13.

19. A method of inducing in a subject an immune response to one dengue virus comprising administering to a subject in need thereof an amount of a composition effective to induce an immune response to one dengue virus serotype wherein said composition comprises (i) a polynucleotide sequence encoding a polypeptide sequence that consists of at least 95% sequence identity to SEQ ID NO: 15, wherein said polypeptide sequence binds to class I WIC molecules to induce a cytotoxic T lymphocyte-mediated immune response, and (ii) a polynucleotide sequence encoding a polypeptide sequence comprising the amino acid sequence of any one of SEQ ID NOs: 2, 3, 4, 5, 6, 7, 8, 9, 10, 11, 12, 14, 16 and 17 or consisting of the amino acid sequence of SEQ ID NOs: 1 or 13.

* * * * *

SEQUENCE LISTING

```
<160> NUMBER OF SEQ ID NOS: 17

<210> SEQ ID NO 1
<211> LENGTH: 9
<212> TYPE: PRT
<213> ORGANISM: Homo sapiens

<400> SEQUENCE: 1

Asn Ile Gln Thr Ala Ile Asn Gln Val
1               5

<210> SEQ ID NO 2
<211> LENGTH: 10
<212> TYPE: PRT
<213> ORGANISM: Homo sapiens

<400> SEQUENCE: 2

Val Thr Leu Leu Cys Leu Ile Pro Thr Val
1               5                   10

<210> SEQ ID NO 3
<211> LENGTH: 9
<212> TYPE: PRT
<213> ORGANISM: Homo sapiens

<400> SEQUENCE: 3

Thr Ile Thr Glu Glu Ile Ala Val Gln
1               5

<210> SEQ ID NO 4
<211> LENGTH: 10
<212> TYPE: PRT
<213> ORGANISM: Homo sapiens

<400> SEQUENCE: 4

Val Leu Gly Trp Leu Glu Lys Tyr Gly Val
1               5                   10

<210> SEQ ID NO 5
<211> LENGTH: 8
<212> TYPE: PRT
<213> ORGANISM: Homo sapiens
```

```
<400> SEQUENCE: 5

Ile Leu Gly Gly Leu Thr Trp Met
1               5

<210> SEQ ID NO 6
<211> LENGTH: 10
<212> TYPE: PRT
<213> ORGANISM: Homo sapiens

<400> SEQUENCE: 6

Lys Ile Leu Ile Gly Ser Val Ile Thr Trp
1               5                   10

<210> SEQ ID NO 7
<211> LENGTH: 11
<212> TYPE: PRT
<213> ORGANISM: Homo sapiens

<400> SEQUENCE: 7

Leu Phe Leu Gly Phe Thr Val Gln Ala Asp Ile
1               5                   10

<210> SEQ ID NO 8
<211> LENGTH: 10
<212> TYPE: PRT
<213> ORGANISM: Homo sapiens

<400> SEQUENCE: 8

Leu Phe Gly Lys Gly Gly Ile Val Thr Arg
1               5                   10

<210> SEQ ID NO 9
<211> LENGTH: 9
<212> TYPE: PRT
<213> ORGANISM: Homo sapiens

<400> SEQUENCE: 9

Ser Pro Ser Arg Leu Ala Ser Ala Ile
1               5

<210> SEQ ID NO 10
<211> LENGTH: 9
<212> TYPE: PRT
<213> ORGANISM: Homo sapiens

<400> SEQUENCE: 10

Ile Pro Ser Glu Asn Glu Val Lys Leu
1               5

<210> SEQ ID NO 11
<211> LENGTH: 9
<212> TYPE: PRT
<213> ORGANISM: Homo sapiens

<400> SEQUENCE: 11

Asn Ile Gln Val Ala Ile Asn Gln Val
1               5

<210> SEQ ID NO 12
<211> LENGTH: 9
<212> TYPE: PRT
<213> ORGANISM: Homo sapiens

<400> SEQUENCE: 12
```

```
Asn Ile Gln Ala Ala Ile Asn Gln Val
1               5

<210> SEQ ID NO 13
<211> LENGTH: 9
<212> TYPE: PRT
<213> ORGANISM: Homo sapiens

<400> SEQUENCE: 13

Val Thr Leu Tyr Leu Gly Val Met Val
1               5

<210> SEQ ID NO 14
<211> LENGTH: 9
<212> TYPE: PRT
<213> ORGANISM: Homo sapiens

<400> SEQUENCE: 14

Val Thr Leu Val Leu Val Gly Ile Val
1               5

<210> SEQ ID NO 15
<211> LENGTH: 9
<212> TYPE: PRT
<213> ORGANISM: Homo sapiens

<400> SEQUENCE: 15

Lys Leu Ala Glu Ala Ile Phe Lys Leu
1               5

<210> SEQ ID NO 16
<211> LENGTH: 15
<212> TYPE: PRT
<213> ORGANISM: Homo sapiens

<400> SEQUENCE: 16

Leu Met Trp Lys Gln Val Thr Pro Glu Leu Asn His Ile Leu Ser
1               5                   10                  15

<210> SEQ ID NO 17
<211> LENGTH: 14
<212> TYPE: PRT
<213> ORGANISM: Homo sapiens

<400> SEQUENCE: 17

Ala Gly Pro Leu Val Ala Gly Gly Met Leu Ile Ala Cys Tyr
1               5                   10
```